United States Patent [19]

Zeeh et al.

[11] 4,411,687
[45] Oct. 25, 1983

[54] α-AZOLYL-GLYCOL DERIVATIVES, AS FUNGICIDES AND PLANT GROWTH REGULATORS

[75] Inventors: Bernd Zeeh, Ludwigshafen; Norbert Goetz, Worms; Eberhard Ammermann, Ludwigshafen; Ernst-Heinrich Pommer, Limburgerhof, all of Fed. Rep. of Germany

[73] Assignee: BASF Aktiengesellschaft, Fed. Rep. of Germany

[21] Appl. No.: 303,572

[22] Filed: Sep. 18, 1981

Related U.S. Application Data

[63] Continuation of Ser. No. 160,309, Jun. 17, 1980, abandoned.

[30] Foreign Application Priority Data

Jun. 29, 1979 [DE] Fed. Rep. of Germany ....... 2926280

[51] Int. Cl.³ .................... A01N 43/50; A01N 43/64; C07D 233/60; C07D 249/08
[52] U.S. Cl. ........................................ 71/76; 71/92; 71/94; 548/101; 548/262; 548/341; 548/247; 548/336; 424/269; 424/273 R; 546/276; 546/278; 252/384
[58] Field of Search ................... 548/101, 341, 262; 424/245, 269, 273 R; 71/92, 76

[56] References Cited

U.S. PATENT DOCUMENTS

| | | | |
|---|---|---|---|
| 3,793,453 | 2/1974 | Godefroi et al. | 548/341 |
| 3,812,142 | 5/1974 | Meiser et al. | 548/341 |
| 3,912,752 | 10/1975 | Meiser et al. | 548/262 |
| 4,005,083 | 1/1977 | Buchel et al. | 548/101 |
| 4,145,428 | 3/1979 | Kramer et al. | 424/245 |
| 4,229,459 | 10/1980 | Kramer et al. | 548/101 |

FOREIGN PATENT DOCUMENTS

| | | | |
|---|---|---|---|
| 502281 | 9/1978 | Australia | 548/262 |
| 2671 | 7/1979 | European Pat. Off. | 548/262 |
| 2063857 | 7/1971 | Fed. Rep. of Germany | 548/341 |
| 2640823 | 3/1977 | Fed. Rep. of Germany | 548/262 |

*Primary Examiner*—Alton D. Rollins
*Attorney, Agent, or Firm*—Keil & Witherspoon

[57] ABSTRACT

α-Azolyl-glycol derivatives of the formula

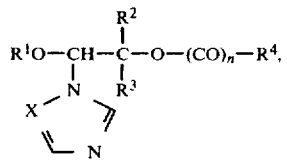

where
$R^1$ is alkyl,
$R^2$ is alkyl or unsubstituted or substituted phenyl,
$R^3$ is hydrogen, alkyl, alkenyl, alkynyl or unsubstituted or substituted benzyl,
$R^4$ is unsubstituted or substituted alkyl, alkenyl, alkynyl, cycloalkyl, cycloalkenyl, arylalkyl or heteroarylalkyl or, where n=1, may also be unsubstituted or substituted aryl or heteroaryl,
X is CH or N and
n is 0 or 1, their salts and metal complexes tolerated by crop plants, their preparation, and agents containing these derivatives for controlling fungi and regulating plant growth.

9 Claims, No Drawings

α-AZOLYL-GLYCOL DERIVATIVES, AS FUNGICIDES AND PLANT GROWTH REGULATORS

This is a continuation of application Ser. No. 160,309, filed June 17, 1980, now abandoned.

The present invention relates to novel α-azolylglycol derivatives, their preparation, fungicidal and growth-regulating agents which contain these active compounds, processes for controlling harmful fungi, and for regulating plant growth, by means of these agents, and the use of the agents for these purposes.

It is known that N,O-acetals containing an O-alkyl radical, eg. 1-(1',2',4'-triazol-1'-yl)-butyl-1-ethyl-ether (German Laid-Open Application DOS No. 2,640,823, Example 4) exhibit fungicidal activity. Other fungicidal ethers have also been disclosed, eg. 1-(2'-(2",4"-dichlorophenyl)-2'-(prop-2"-enyloxy)-ethyl)-1H-imidazole (German Laid-Open Application DOS No. 2,063,857). However, they are insufficiently active, in particular against rust fungi and mildew fungi. They are therefore not very suitable for controlling fungi harmful to crops and materials.

The invention relates to α-azolyl-glycol derivatives of the general formula I

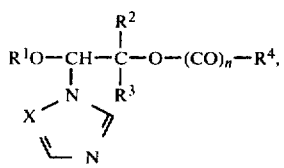

where
R$^1$ is alkyl,
R$^2$ is alkyl or unsubstituted or substituted phenyl,
R$^3$ is hydrogen, alkyl, alkenyl, alkynyl or unsubstituted or substituted benzyl,
R$^4$ is unsubstituted or substituted alkyl, alkenyl, alkynyl, cycloalkyl, cycloalkenyl, arylalkyl or heteroarylalkyl or, where n=1, may also be unsubstituted or, substituted aryl or heteroaryl,
X is CH or N and
n is 0 or 1, and their salts and metal complexes tolerated by crop plants.

In formula I, R$^1$ preferably is branched or unbranched alkyl of 1 to 4 carbon atoms, ie. methyl, ethyl, n-propyl, isopropyl, n-butyl, isobutyl or tert.-butyl.

R$^2$ is preferably alkyl of 1 to 6 carbon atoms, which may be unbranched, eg. methyl, ethyl, propyl, butyl or pentyl, or may be branched and of 3 to 6 carbon atoms, eg. isopropyl, tert.-butyl or 3-methyl-but-1-yl. R$^2$ may also be phenyl which is unsubstituted or is monosubstituted or disubstituted by halogen, preferably by chlorine.

R$^3$ is preferably hydrogen, unbranched alkyl of 1 to 6 carbon atoms, eg. methyl, ethyl, n-propyl, n-butyl or n-pentyl, branched alkyl of 3 to 6 carbon atoms, eg. isopropyl or isobutyl, alkenyl or alkynyl of 2 to 6 carbon atoms, eg. vinyl, ethynyl, prop-2-en-1-yl, prop-2-yn-1-yl or 3-methyl-but-2-en-1-yl, or benzyl which is unsubstituted or is monosubstituted or disubstituted by halogen, eg. by fluorine or chlorine.

R$^4$ preferably is unsubstituted or substituted alkyl of up to 10 carbon atoms, and may be unbranched, eg. methyl, ethyl, n-propyl, n-pentyl or n-decyl, or branched, eg. isopropyl, 2-methylprop-1-yl or 3,3-dimethyl-n-but-1-yl, unbranched or branched alkenyl or alkynyl of up to 10 carbon atoms, eg. prop-2-en-1-yl, prop-2-yn-1-yl or penta-1,3-dien-1-yl, or cycloalkyl or cycloalkenyl of 5 or 6 ring carbon atoms, eg. cyclopentyl, cyclohex-2-en-1-yl or cyclohexyl, as well as unsubstituted or substituted arylalkyl or heteroarylalkyl, where alkyl is of 1 or 2 carbon atoms, aryl is of 6 to 12 carbon atoms and heteroaryl is of 5 or 6 ring members, of which 1 to 3 may be hetero-atoms, eg. oxygen, nitrogen or sulfur. Examples of the latter group of radicals are unsubstituted or substituted benzyl, phenylethyl, naphthylmethyl, thienylmethyl and isoxazolylmethyl.

Where n is 1, R$^4$ may also be unsubstituted or substituted aryl or heteroaryl. Examples thereof are phenyl, naphthyl, and 5-membered or 6-membered heterocyclic radicals containing 1 or 2 hetero-atoms, eg. furanyl, thienyl, pyridyl and isoxazolyl.

Specific examples of substituents in the radicals R$^4$ are halogen, eg. fluorine, chlorine, bromine and iodine, nitro or cyano, lower alkyl, haloalkyl, alkoxy, alkylthio and haloalkoxy, of 1 to 4 carbon atoms and, where relevant, of 1 to 9 halogen atoms, eg. methyl, trifluoromethyl, methoxy, methylthio, ethyl, ethoxy, tetrafluoroethoxy, n-propyl and tert.-butyl, or keto groups, as for example in a phenacyl radical.

The novel α-azolyl-glycol derivatives possess a center of asymmetry in the acetal carbon atom and, if R$^2$ and R$^3$ are different, also in the carbinol carbon atom. Depending on the nature of R$^4$, other centers of asymmetry may also be present. The compounds can be obtained in the form of single enantiomers or diastereomers by conventional methods of separation. In practice, either the individual enantiomers and diastereomers, or the mixtures usually obtained on synthesis, may be used, the latter being preferred.

The novel α-azolyl-glycol derivatives of the formula I may be prepared by the following methods:

(a) an alcohol of the formula II

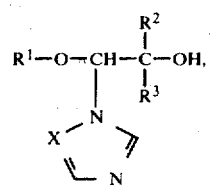

where R$^1$, R$^2$, R$^3$ and X have the above meanings, or an alkali metal salt or quaternary ammonium salt thereof, is reacted with a compound of the formula III

where R$^4$ and n have the above meanings and L is a nucleophilically displaceable leaving group, in the presence or absence of a solvent or diluent and/or of an inorganic or organic base and in the presence or absence of a reaction accelerator, at from 0° to 120° C.

(b) An acetal of the formula IV

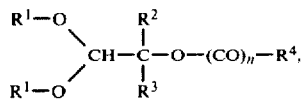

where $R^1$, $R^2$, $R^3$, $R^4$ and n have the above meanings, is reacted first with acetyl chloride or acetyl bromide and then with an azole of the formula V

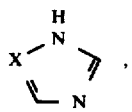   V where X is CH or N, or with an alkali metal salt or alkaline earth metal salt thereof, in the presence or absence of a solvent or diluent and/or of an inorganic or organic base, at from 0° to 100° C.

The alcohols of the formula II, used as the starting material for process (a), may be prepared by, for example, the following methods:

1. A ketone of the formula VI

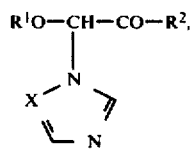   VI where $R^1$, $R^2$ and X have the above meanings, is reduced catalytically, or with a complex hydride, in the presence of a solvent and in the presence or absence of a reaction accelerator at from 0° to 100° C.

Compounds VI may be prepared by reacting an α-haloether of the formula VII $$R^1O-\underset{Hal}{CHCO}-R^2,$$   VII where $R^1$ and $R^2$ have the above meanings and Hal is chlorine or bromine, with an azole of the formula V or an alkali metal salt or alkaline earth metal salt thereof, in the presence of a solvent and of a base, at from 0° to 100° C.

α-Haloethers of the formula VII can be prepared by conventional methods (cf. German Laid-Open Application DOS 2,201,063 and B. Mylo, Chem. Ber. 44 (1911), 3212, and Straus and Weber, Ann. 498 (1932), 124).

2. A ketone of the formula VI is reacted with a Grignard reagent of the formula VIII

   VIII, where $R^3$ has the above meanings, in the presence of an inert solvent, at from 0° to 80° C.

3. An acetal of the formula IX

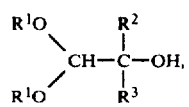   IX where $R^1$, $R^2$ and $R^3$ have the above meanings, is reacted with acetyl chloride or acetyl bromide and subsequently with an azole of the formula V in the presence of a solvent and of a base, at from 0° to 100° C.

The compounds of the formula III are known. In formula III, L may be, for example, halogen, eg. chlorine, bromine or iodine, alkyl-sulfate, unsubstituted or substituted alkylsulfonyloxy, eg. methanesulfonyloxy or trifluoromethanesulfonyloxy, or arylsulfonyloxy, eg. tosylate. Other examples of nucleophilically displaceable leaving groups, especially for the reactive acid derivatives of the formula III, are azolyl groups, eg. imidazolyl or triazolyl, and acyloxy groups, as in the case of acid anhydrides.

Examples of suitable inorganic or organic bases, which may if desired also be used as acid acceptors in process A or B, are alkali metal hydroxides and alkaline earth metal hydroxides, eg. sodium hydroxide, potassium hydroxide and calcium hydroxide, alkali metal carbonates, eg. potassium carbonate and sodium carbonate, alkali metal hydrides, eg. sodium hydride, alkali metal alcoholates and alkaline earth metal alcoholates, eg. sodium methylate, magnesium methylate and sodium isopropylate, and tertiary amines, eg. trimethylamine, triethylamine, N,N-dimethylaniline, N,N-dimethylcyclohexylamine, N-methylpiperidine and pyridine. However, other conventional bases may also be used.

It is also possible first to convert the alcohols of the formula II into alcoholate salts by means of suitable bases, for example an alkali metal hydride, eg. sodium hydride, or a lithium alkyl, eg. butyl-lithium, or an alkali metal alcoholate or alkaline earth metal alcoholate, eg. sodium methylate, after which they are employed, as salts, in the reaction.

The preferred solvents and diluents include halohydrocarbons, eg. methylene chloride, chloroform, 1,2-dichloroethane and chlorobenzene, aliphatic and aromatic hydrocarbons, eg. cyclohexane, petroleum ether, benzene, toluene and xylenes, esters, eg. ethyl acetate, amides, eg. dimethylformamide, nitriles, eg. acetonitrile, sulfoxides, eg. dimethylsulfoxide, ketones, eg. acetone and methyl ethyl ketone, ethers, eg. diethyl ether, tetrahydrofuran and dioxane, and mixtures of the above.

Preferred reaction accelerators are metal halides, eg. potassium iodide, crown ethers, quaternary ammonium compounds, eg. tetrabutylammonium iodide, acids and combinations of the said accelerators.

The acetals of the formula IV employed as a starting material in process (b) can be prepared in accordance with conventional methods by reacting an alcohol of the formula X

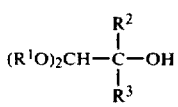   X with a compound of the formula III.

Some of the alcohols of the formula X are known, as, for example, 1,1-dimethoxy-2-methylbut-3-yn-2-ol (German Pat. No. 1,768,877) or 1,1-dimethoxy-2-methylbut-3-en-2-ol (German Pat. No. 1,115,238). However, they can also be prepared by conventional methods, wherein a ketone of the formula XI $$(R^1O)_2CH-CO-R^2$$   XI is hydrogenated catalytically or with a complex hydride, or is reacted with a Grignard reagent of the formula VIII.

To prepare the novel α-azolyl-glycol derivatives of the formula I by process (b), the reaction of the acetal of the formula IV with acetyl chloride or acetyl bromide is advantageously carried out in the absence of a solvent or in an inert solvent or diluent, eg. ether, methylene chloride, chloroform, cyclohexane or toluene. The reaction temperature may be from 20° to 100° C. and depends on the radical OR¹.

The reaction of the α-haloether, formed as an intermediate, with an azole of the formula V is advantageously carried out in a solvent or diluent, eg. methylene chloride, chloroform, 1,2-dichloroethane, chlorobenzene, an aliphatic or aromatic hydrocarbon, eg. cyclohexane, petroleum ether, benzene, toluene or xylenes, an ester, eg. ethyl acetate, an amide, eg. dimethylformamide, a nitrile, eg. acetonitrile, a sulfoxide, eg. dimethylsulfoxide, a ketone, eg. acetone or methyl ethyl ketone, an ether, eg. diethyl ether, tetrahydrofuran or dioxane, or a mixture of these.

Examples of suitable inorganic or organic bases which may if desired also be employed as acid acceptors in process (b) are alkali metal hydroxides and alkaline earth metal hydroxides, eg. sodium hydroxide, potassium hydroxide and calcium hydroxide, alkali metal carbonates, et. potassium carbonate and sodium carbonate, alkali metal hydrides, eg. sodium hydride, alkali metal alcoholates and alkaline earth metal alcoholates, eg. sodium methylate, magnesium methylate and sodium isopropylate, tertiary amines, eg. trimethylamine, triethylamine, N,N-dimethylaniline, N,N-dimethylcyclohexylamine, N-methylpiperidine and pyridine, and azoles, eg. 1,2,4-triazole and imidazole. However, other conventional bases may also be used.

It is also possible, in a preliminary reaction, first to convert the azole of the formula V into a salt by means of a suitable base, for example an alkali metal hydride, eg. sodium hydride, a lithium-alkyl, eg. butyllithium, or an alkali metal alcoholate or alkaline earth metal alcoholate, eg. sodium methylate, the salt then being employed in the reaction.

The reactions according to the invention are in general carried out at from 0° to 150° C., for from 1 to 60 hours, under atmospheric or superatmospheric pressure, continuously or batchwise.

The conventional methods are used to isolate the compounds according to the invention. In general, the products obtained do not require further purification, but where required such purification can be carried out by conventional methods, such as recrystallization, extraction, distillation or chromatography.

If desired, the α-azolyl-glycol derivatives of the formula I are subsequently converted, by conventional processes, to their salts or metal complexes which are tolerated by crop plants.

Examples of suitable salifying agents are hydrochloric acid, hydrobromic acid, sulfuric acid, nitric acid, phosphoric acid, acetic acid and dodecylbenzenesulfonic acid. The activity of the salts depends on the cation, so that any anion may be chosen.

Metal complexes are formed by an addition reaction of the novel compounds with the cations of metal salts. Particularly suitable metal salts are copper (II) chloride, copper(II) sulfate, copper(II) nitrate, zinc(II) chloride, iron(III) chloride, manganese(II) chloride and nickel-(II) bromide.

The Examples which follow illustrate the preparation of the novel substances. Preparation of the starting materials (a) Process 1

36.8 g of acetyl bromide are added dropwise, whilst stirring, to 48 g of 1,1-dimethoxy-3,3-dimethylbutan-2-one (cf. J. B. Wright, J. Am. Chem. Soc. 77 (1955), 4883). In the course thereof, the temperature rises to 53° C. After the solution has been stirred for one hour, it is added dropwise to a solution of 41.4 g of triazole in 100 ml of dimethylformamide and 100 ml of tetrahydrofuran. The reaction mixture is stirred for three hours and is then concentrated; the residue is taken up in methylene chloride and this solution is washed with three 50 ml portions of water. The organic phase is separated off, dried and concentrated. The oil which remains is distilled through a column. 44 g of 1-(1',2',4'-triazol-1'-yl)-1-methoxy-3,3-dimethylbutan-2-one pass over at 84°–88° C./0.1 mbar.

4.5 g of sodium borohydride are added, in portions, to 39.4 g of the compound obtained above, in 80 ml of methanol, at 10°–20° C. The reaction mixture is then stirred for 1 hour under reflux, after which it is stirred into 80 ml of water, and the batch is extracted with three 100 ml portions of methylene chloride. The organic phase is separated off, dried and concentrated. The oil which is left crystallizes out from petroleum ether. This gives 34 g of 1-(1',2',4'-triazol-1'-yl)-1-methoxy-3,3-dimethylbutan-2-ol, of melting point 62°–64° C.

|  | C | H | N |
|---|---|---|---|
| calculated | 54.3 | 8.6 | 21.1 |
| found | 54.5 | 8.4 | 21.2 |

A solution of 1-(1',2',4'-triazol-1'-yl)-1-methoxyacetone in 100 ml of ether is added dropwise to a solution of 0.2 mole of 4-chlorophenyl-magnesium bromide (prepared from 4.9 g of magnesium and 38.3 g of 4-bromochlorobenzene) in 150 ml of ether. The reaction mixture is then stirred for 5 hours under reflux, after which it is cooled. 50 g of ice are introduced, and 25% strength aqueous ammonium chloride solution is then added dropwise until the phases separate clearly. The organic phase is separated off and the aqueous phase is extracted with twice 100 ml of ether. The combined ether phases are washed neutral with water, dried and concentrated. The residue is recrystallized from petroleum ether, giving 23 g of crystalline 1-(1',2',4'-triazol-1'-yl)-1-methoxy-2-(4'-chlorophenyl)-propan-2-ol, of melting point 80°–82° C.

(c) Process 3

12.3 g of acetyl bromide are added dropwise to 14.8 g of 1,1-(dimethoxy)-2-methylbutan-2-ol, whilst stirring; in the course thereof, the temperature rises to 60° C. After the reaction mixture has been stirred for one hour, it is added dropwise to a solution of 13.8 g of triazole in 100 ml of tetrahydrofuran and 50 ml of dimethylformamide. The reaction mixture is then stirred overnight, concentrated and taken up in methylene chloride, and the solution is washed with three 50 ml portions of water. The organic phase is dried and concentrated. The oil which remains is distilled. 6 g of 1-(1',2',4'-triazol-1'-yl)-1-methoxy-2-methylbutan-2-ol pass over at 95°–110° C./0.4 mbar.

All the alcohols of the formula II can be prepared by methods similar to (a), (b) and (c). Preparation of the end products EXAMPLE 1 (Process a)

A solution of 13.9 g of 1-(1',2',4'-triazol-1'-yl)-1-methoxy-3,3-dimethylbutan-2-ol in 30 ml of tetrahydrofuran is added dropwise to a suspension of 2 g of sodium hydride in 80 ml of tetrahydrofuran at room temperature. The mixture is stirred for three hours and 12 g of benzyl bromide are then added dropwise. Thereafter the batch is stirred overnight, 100 ml of water are added, the organic phase is separated off and the aqueous phase is extracted twice with diethyl ether. The combined ether phases are dried and concentrated. The oil which remains is distilled. 9.7 g of 1-(1',2',4'-triazol-1'-yl)-1-methoxy-3,3-dimethylbut-2-yl benzyl ether pass over at 132°-135° C./0.007 mbar.

|  | C | H | N |
|---|---|---|---|
| calculated | 66.4 | 8.0 | 14.5 |
| found | 66.6 | 8.2 | 15.0 |

EXAMPLE 2 (Process a)

A solution of 7.9 g of 1-(1',2',4'-triazol-1'-yl)-1-methoxy-propan-2-ol in 50 ml of dimethylformamide is added dropwise to a suspension of 1.44 g of sodium hydride in 100 ml of tetrahydrofuran. The mixture is then refluxed for two hours. When it has cooled to room temperature, 6.4 ml of benzoyl chloride are added dropwise, in the course of which the temperature rises to 50° C. After two hours, 150 ml of water are added and the mixture is extracted with three 150 ml portions of ether. The combined ether phases are washed neutral with water, dried and concentrated. The oil which remains crystallizes from petroleum ether. 8 g of 1-(1',2',4'-triazol-1'-yl)-1-methoxyprop-2-yl benzoate, of melting point 76°-78° C., are obtained.

|  | C | H | N |
|---|---|---|---|
| calculated | 59.8 | 5.8 | 16.1 |
| found | 59.8 | 5.8 | 16.1 |

EXAMPLE 3 (Process b)

12.3 g of acetyl bromide are added dropwise to 17.6 g of 1,1-dimethoxy-3,3-dimethyl-but-2-yl methyl ether, in the course of which the temperature rises to 55° C. After the solution has been stirred for one hour, it is added dropwise to a solution of 13.8 g of triazole in 50 ml of dimethylformamide and 50 ml of tetrahydrofuran. After three hours, the reaction mixture is concentrated, the residue is taken up in 200 ml of methylene chloride, and this solution is extracted by shaking with three 50 ml portions of water. The organic phase is separated off, dried and concentrated. The oil which remains is distilled. 7.4 g of 1-(1',2',4'-triazol-1'-yl)-1-methoxy-3,3-dimethylbut-2-yl methyl ether pass over at 75°-77° C./0.3 mbar.

|  | C | H | N |
|---|---|---|---|
| calculated | 56.3 | 9.0 | 19.7 |
| found | 56.6 | 9.0 | 20.1 |

The following α-azolyl-glycol derivatives of the formula I may be prepared by similar methods.

TABLE 1

| No. | $R^1$ | $R^2$ | $R^3$ | $R^4$ | n | X | b.p. °C./mbar |
|---|---|---|---|---|---|---|---|
| 4 | $CH_3$ | $CH_2-CH_2-CH(CH_3)_2$ | H | $CH_3$ | 0 | N | 103-105/0.7 |
| 5 | $CH_3$ | $CH_2-CH_2-CH(CH_3)_2$ | H | $CH_3$ | 0 | CH | 108-110/0.7 |
| 6 | $CH_3$ | $CH_3$ | H | $4-Cl-C_6H_4$ | 1 | N | m.p. 53-55 |
| 7 | $CH_3$ | $CH_3$ | $C_2H_5$ | $CH_3$ | 0 | N | 88-90/0.5 |
| 8 | $CH_3$ | $CH_3$ | $C_2H_5$ | $CH_3$ | 0 | CH | 93-95/0.5 |
| 9 | $CH_3$ | $CH_3$ | $CH=CH_2$ | $CH_3$ | 0 | N | 83-85/0.1 |
| 10 | $CH_3$ | $CH_3$ | $CH=CH_2$ | $CH_3$ | 0 | CH | 98-100/0.4 |
| 11 | $CH_3$ | $CH_3$ | $C\equiv CH$ | $CH_3$ | 0 | N | 93-95/0.5 |
| 12 | $CH_3$ | $CH_3$ | $C\equiv CH$ | $CH_3$ | 0 | CH | 108-110/0.5 |
| 13 | $CH_3$ | $CH_3$ | $CH=CH_2$ | $CH_2-CH=CH_2$ | 0 | N | 100-105/0.7 |
| 14 | $CH_3$ | $CH_3$ | $CH=CH_2$ | $CH_2-CH=CH_2$ | 0 | CH | 105-110/0.7 |
| 15 | $CH_3$ | $CH_3$ | $C\equiv CH$ | $CH_2-CH=CH_2$ | 0 | N | 110-115/0.7 |
| 16 | $CH_3$ | $CH_3$ | $C\equiv CH$ | $CH_2-CH=CH_2$ | 0 | CH | 125-130/0.4 |
| 17 | $CH_3$ | $CH_3$ | $CH=CH_2$ | $CH_2-p-Cl-C_6H_4$ | 0 | N | 160-165/0.3 |
| 18 | $CH_3$ | $CH_3$ | $CH=CH_2$ | $CH_2-p-Cl-C_6H_4$ | 0 | CH | 150-160/0.1 |
| 19 | $CH_3$ | $CH_3$ | $C\equiv CH$ | $CH_2-p-Cl-C_6H_4$ | 0 | N | 140-150/0.1 |
| 20 | $CH_3$ | $CH_3$ | $C\equiv CH$ | $CH_2-p-Cl-C_6H_4$ | 0 | CH | 155-165/0.1 |
| 21 | $CH_3$ | $CH_3$ | $C\equiv CH$ | $CH_3$ | 1 | N | 130-135/0.5 |
| 22 | $CH_3$ | $C_6H_5$ | $CH_3$ | $CH_3$ | 0 | N | oil |
| 23 | $CH_3$ | $4-Cl-C_6H_4$ | $CH_3$ | $CH_3$ | 0 | N | m.p. 112-114 |
| 24 | $CH_3$ | $4-Cl-C_6H_4$ | $CH_3$ | $CH_2CH=CH_2$ | 0 | N | m.p. 78-80 |
| 25 | $CH_3$ | $4-Cl-C_6H_4$ | $CH_3$ | $CH-p-Cl-C_6H_4$ | 0 | N | m.p. 148-149 |
| 26 | $CH_3$ | $tert-C_4H_9$ | H | $CH_3$ | 0 | CH | 85-88/0.01 |
| 27 | $CH_3$ | $tert-C_4H_9$ | H | $CH_2-CH=CH_2$ | 0 | N | 82-85/0.1 |
| 28 | $CH_3$ | $tert-C_4H_9$ | H | $CH_2-CH=CH_2$ | 0 | CH |  |
| 29 | $CH_3$ | $tert-C_4H_9$ | H | $CH_2-C_6H_5$ | 0 | N | 132-135/0.007 |
| 30 | $CH_3$ | $tert-C_4H_9$ | H | $CH_2-C_6H_5$ | 0 | CH |  |
| 31 | $CH_3$ | $tert-C_4H_9$ | H | $CH_2-p-Cl-C_6H_4$ | 0 | N | 156-158/0.04 |
| 32 | $CH_3$ | $tert-C_4H_9$ | H | $CH_2-p-Cl-C_6H_4$ | 0 | CH |  |
| 33 | $CH_3$ | $tert-C_4H_9$ | H | $CH_2-2,4-Cl_2-C_6H_3$ | 0 | N | oil |
| 34 | $CH_3$ | $tert-C_4H_9$ | H | $CH_2-2,4-Cl_2-C_6H_3$ | 0 | CH |  |
| 35 | $CH_3$ | $tert-C_4H_9$ | $CH_3$ | $CH_3$ | 0 | N | 82-86/0.1 |
| 36 | $CH_3$ | $tert-C_4H_9$ | $CH=CH_2$ | $CH_3$ | 0 | N | 89-92/0.1 |
| 37 | $CH_3$ | $tert-C_4H_9$ | $CH_3$ | $CH_2-CH=CH_2$ | 0 | N | 98-100/0.3 |
| 38 | $CH_3$ | $tert-C_4H_9$ | $CH=CH_2$ | $CH_2-C\equiv CH$ | 0 | N | m.p. 70-72 |
| 39 | $CH_3$ | $tert-C_4H_9$ | $CH_3$ | $CH_2-p-Cl-C_6H_4$ | 0 | N | m.p. 73-75 |
| 40 | $CH_3$ | $tert-C_4H_9$ | $CH=CH_2$ | $CH_2-C_6H_5$ | 0 | N |  |
| 41 | $CH_3$ | $CH_3$ | H | $CH_3$ | 0 | N | 74-75/0.2 |
| 42 | $CH_3$ | $CH_3$ | H | $C_2H_5$ | 0 | N |  |
| 43 | $CH_3$ | $CH_3$ | H | $CH_2CH=CH_2$ | 0 | N | 82-85/0.2 |
| 44 | $CH_3$ | $CH_3$ | H | $CH_2C\equiv CH$ | 0 | N |  |
| 45 | $CH_3$ | $CH_3$ | H | $CH_2-C_6H_5$ | 0 | N | oil |

TABLE 1-continued

| No. | R¹ | R² | R³ | R⁴ | n | X | b.p. °C./mbar |
|---|---|---|---|---|---|---|---|
| 46 | CH₃ | CH₃ | H | CH₂—p-Cl—C₆H₄ | 0 | N | oil |
| 47 | CH₃ | CH₃ | H | CH₃ | 0 | CH | 75-84/0.4 |
| 48 | CH₃ | CH₃ | H | CH₂—CH=CH₂ | 0 | CH | 86-89/0.2 |
| 49 | CH₃ | CH₃ | H | CH₂—p-Cl—C₆H₄ | 0 | CH | oil |
| 50 | CH₃ | CH₃ | H |  | 1 | N | m.p. 51-52 |
| 51 | CH₃ | CH₃ | H | 3,5-Cl₂—C₆H₃ | 1 | N | m.p. 90-91 |
| 52 | CH₃ | CH₃ | H | 3-NO₂—C₆H₄ | 1 | N | m.p. 85-87 |
| 53 | CH₃ | CH₃ | H | 2-CF₃—C₆H₄ | 1 | N | 134-137/0.007 |
| 54 | CH₃ | CH₃ | H | CH₃ | 1 | CH | |
| 55 | n-C₄H₉ | tert-C₄H₉ | H | CH₂—C₆H₅ | 0 | N | oil |
| 56 | n-C₄H₉ | tert-C₄H₉ | H | CH₂—p-Cl—C₆H₄ | 0 | N | oil |
| 57 | CH₃ | tert-C₄H₉ | CH₂—C₆H₅ | CH₃ | 0 | N | m.p. 95-97 |
| 58 | CH₃ | tert-C₄H₉ | CH₂—p-Cl—C₆H₄ | CH₃ | 0 | N | m.p. 115-117 |
| 59 | CH₃ | tert-C₄H₉ | CH₂—C₆H₅ | CH₂—CH=CH₂ | 0 | N | m.p. 115 |
| 60 | CH₃ | tert-C₄H₉ | CH₂—p-Cl—C₆H₄ | CH₂—CH=CH₂ | 0 | N | m.p. 152 |
| 61 | n-C₄H₉ | tert-C₄H₉ | CH₃ | CH₂—C₆H₅ | 0 | N | |
| 62 | n-C₄H₉ | tert-C₄H₉ | CH₃ | CH₂—p-Cl—C₆H₄ | 0 | N | oil |
| 63 | CH₃ | CH₃ | H | 4-Cl—C₆H₅ | 1 | CH | |
| 64 | CH₃ | 2,4-Cl₂—C₆H₃ | H | CH₃ | 0 | N | m.p. 92-94 |
| 65 | CH₃ | 2,4-Cl₂—C₆H₃ | H | CH₂—CH=CH₂ | 0 | N | oil |
| 66 | CH₃ | 2,4-Cl₂—C₆H₃ | H | CH₂—p-Cl—C₆H₄ | 0 | N | m.p. 95-110 |
| 67 | C₂H₅ | 2,4-Cl₂—C₆H₃ | H | CH₃ | 0 | N | m.p. 85-87 |
| 68 | C₂H₅ | 2,4-Cl₂—C₆H₃ | H | CH₂—CH=CH₂ | 0 | N | oil |
| 69 | C₂H₅ | 2,4-Cl₂—C₆H₃ | H | CH₂—C₆H₅ | 0 | N | |
| 70 | CH₃ | C₆H₅ | CH₃ | CH₂—CH=CH₂ | 0 | N | oil |
| 71 | CH₃ | C₆H₅ | CH₃ | CH₂—p-Cl—C₆H₄ | 0 | N | m.p. 128-130 |
| 72 | n-C₄H₉ | 4-Cl—C₆H₄ | CH₃ | CH₃ | 0 | N | 143-149/0.0015 |
| 73 | n-C₄H₉ | 4-Cl—C₆H₄ | CH₃ | CH₂—CH=CH₂ | 0 | N | 147-152/0.0015 |
| 74 | n-C₄H₉ | 4-Cl—C₆H₄ | CH₃ | CH₂—p-Cl—C₆H₄ | 0 | N | 205-218/0.015 |
| 75 | iso-C₄H₉ | 4-Cl—C₆H₄ | CH₃ | CH₃ | 0 | N | 142-148/0.0015 |
| 76 | iso-C₄H₉ | 4-Cl—C₆H₄ | CH₃ | C₂H₅ | 0 | N | 151-156/0.0015 |
| 77 | iso-C₄H₉ | 4-Cl—C₆H₄ | CH₃ | CH₂—C₆H₅ | 0 | N | 185-198/0.005 |
| 78 | CH₃ | p-C₆H₅—C₆H₄ | CH₃ | CH₃ | 0 | N | m.p. 163-165 |
| 79 | CH₃ | p-C₆H₅—C₆H₄ | CH₃ | CH₂—CH=CH₂ | 0 | N | m.p. 85-87 |
| 80 | CH₃ | p-C₆H₅—C₆H₄ | CH₃ | CH₂—p-Cl—C₆H₄ | 0 | N | m.p. 103-105 |
| 81 | CH₃ | CH₃ | CH₂—p-Cl—C₆H₄ | CH₃ | 0 | N | |
| 82 | CH₃ | CH₃ | CH₂—p-Cl—C₆H₄ | CH₂—CH=CH₂ | 0 | N | |
| 83 | CH₃ | CH₃ | CH₂—p-Cl—C₆H₄ | CH₂—p-Cl—C₆H₄ | 0 | N | |
| 84 | CH | 2,4-Cl₂—C₆H₃ | CH₃ | CH₃ | 0 | N | m.p. 98-94 |
| 85 | CH₃ | 2,4-Cl₂—C₆H₃ | CH₃ | CH₂—CH=CH₂ | 0 | N | oil |
| 86 | CH₃ | 2,4-Cl₂—C₆H₃ | CH₃ | CH₂—C₆H₅ | 0 | N | oil |
| 87 | C₂H₅ | 2,4-Cl₂—C₆H₃ | CH₃ | CH₃ | 0 | N | m.p. 57-59 |
| 88 | C₂H₅ | 2,4-Cl₂—C₆H₃ | CH₃ | CH₂—CH=CH₂ | 0 | N | m.p. 79-80 |
| 89 | tert-C₄H₉ | CH₃ | H | CH₃ | 0 | N | |
| 90 | tert-C₄H₉ | CH₃ | H | CH₂—CH=CH₂ | 0 | N | |
| 91 | tert-C₄H₉ | CH₃ | H | CH₂—p-Cl—C₆H₄ | 0 | N | |
| 92 | tert-C₄H₉ | CH₃ | CH₃ | CH₂—C₆H₅ | 0 | N | |
| 93 | tert-C₄H₉ | CH₃ | CH₃ | CH₂—p-Cl—C₆H₄ | 0 | N | |
| 94 | tert-C₄H₉ | C₆H₅ | CH₃ | CH₃ | 0 | N | |
| 95 | tert-C₄H₉ | C₆H₅ | CH₃ | CH₂—CH=CH₂ | 0 | N | |
| 96 | tert-C₄H₉ | C₆H₅ | CH₃ | CH₂—p-Cl—C₆H₄ | 0 | N | |
| 97 | tert-C₄H₉ | 4-Cl—C₆H₄ | CH₃ | CH₃ | 0 | N | |
| 98 | tert-C₄H₉ | 4-Cl—C₆H₄ | CH₃ | CH₂—CH=CH₂ | 0 | N | |
| 99 | tert-C₄H₉ | 4-Cl—C₆H₄ | CH₃ | CH₂—p-Cl—C₆H₄ | 0 | N | |
| 100 | tert-C₄H₉ | tert-C₄H₉ | CH₃ | CH₃ | 0 | N | |
| 101 | tert-C₄H₉ | tert-C₄H₉ | CH₃ | CH₂—CH=CH₂ | 0 | N | |
| 102 | tert-C₄H₉ | tert-C₄H₉ | CH₃ | CH₂—p-Cl—C₆H₄ | 0 | N | |

The compounds according to the invention and their salts and metal complexes are good plant treatment agents. For instance, they have an excellent action on a broad spectrum of plant-pathogenic fungi, particularly from the Ascomycetes and Basidiomycetes classes. Some of them have a systemic action and may be used as foliar and soil fungicides, and also as seed disinfectants. The agents may also be used to protect materials.

The fungicidal compounds are of particular interest for combating numerous fungi in various crop plants or their seed, especially wheat, rye, barley, oats, rice, Indian corn, cotton, soybeans, coffee, sugarcane, fruit and ornamentals in horticulture, and vegetables such as cucumbers, beans and Cucurbitaceae.

The new compounds are especially suitable for combatting the following diseases: Erysiphe graminis in cereals, Erysiphe cichoriacearum in Cucurbitaceae, Podosphaera leucotricha in apples, Uncinula necator in grapes, Erysiphe polygoni in beans, Sphaerotheca pannosa in roses, Puccinia species in cereals, Rhizoctonia solani in cotton, Helminthosporium species in cereals, Ustilago species in cereals and sugarcane, Rhynchosporium secale in cereals and Venturia inaequalis in apples.

The compounds are applied by spraying or dusting the plants with the active ingredients, or treating seed with them. The compounds may be applied before or after the plants or seed have been infected by fungi.

The active ingredients of the invention can be converted into the conventional formulations, e.g. solutions, emulsions, suspensions, dusts, powders, pastes and granules. The form of application depends entirely on the purpose for which the agent is to be used; at all events, it should ensure a fine and uniform distribution of the active ingredient. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxilaries are, essentially, solvents, for example aromatics, e.g. xylene and benzene, chloroaromatics, e.g. chlorobenzene, paraffins, e.g. petroleum fractions, alcohols, e.g. methanol and butanol, amines, e.g. ethanolamine and dimethylformamide, and water; carriers, for example natural rock powders, e.g. kaolin, alumina, talc and chalk, and synthetic rock powders, e.g. highly disperse silica and silicates; emulsifiers; for example non-ionic and anionic emulsifiers, e.g. polyoxyethylene fatty alcohol ethers, alkylsulfonates and arylsulfonates, and dispersants, for example lignin, sulfite waste liquors and methylcellulose.

The fungicidal agents contain from 0.1 to 95% (by weight) of active ingredient, preferably from 0.5 to 90%. The application rates depend on the effect desired, and are from 0.1 to 3 kg and more of active ingredient per hectare. The new compounds may also be used for protecting materials, inter alia for combating wood-destroying fungi such as Coniophora puteanea and Polystictus versicolor. When the active ingredients are used for protecting materials, e.g., as fungicides for paints and soft PVC, the application rates are from 0.05 to 5% (wt%) of active ingredient, based on the total weight of the paint to be preserved or the PVC to be microbicidally treated. The new active ingredients may also be used as fungicidally effective compounds of oily wood preservatives for protecting wood against discoloring fungi. The agents are applied by treating the wood with them, e.g., by impregnation or painting.

The agents, and the ready-to-use preparation obtained therefrom, e.g., solutions, emulsions, suspensions, powders, dusts, pastes or granules, are applied in the conventional manner, e.g. by spraying, atomizing, dusting, treating seed, or watering.

Examples of such preparations are given below.

I. 90 parts by weight of the compound of Example 1 is mixed with 10 parts by weight of N-methyl-α-pyrrolidone. A mixture is obtained which is suitable for application in the form of very fine drops.

II. 20 parts by weight of the compound of Example 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

III. 20 parts by weight of the compound of Example 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IV. 20 parts by weight of the compound of Example 5 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

V. 20 parts by weight of the compound of Example 6 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of the compound of Example 1 is intimately mixed with 97 parts by weight of particulate kaolin. A dust is obtained containing 3% by weight of the active ingredient.

VII. 30 parts by weight of the compound of Example 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of the compound of Example 3 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

IX. 20 parts of the compound of Example 4 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The agents according to the invention may be mixed and applied with other active ingredients, e.g. herbicides, insecticides, growth regulators and other fungicides or may be mixed with fertilizers and applied together with these. Mixtures with other fungicides often broadens the spectrum of fungicidal action.

The following list of fungicides with which the compounds according to the invention may be combined is intended to illustrate and not restrict the combination possibilities. Examples of fungicides which can be combined with the compounds of the invention are: sulfur, dithiocarbamates and their derivatives, e.g. iron(III) dimethyldithiocarbamate, zinc dimethyldithiocarbamate, manganese N,N-ethylene-bis-dithiocarbamate, manganese zinc N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and zinc N,N'-propylene-bis-dithiocarbamate, and the ammonia complex of zinc N,N'-propylene-bis-dithiocarbamate and N,N'-polypropylene-bis-(thiocarbamoyl)-disulfide; nitro derivatives, e.g. dinitro-(1-methylheptyl)-phenyl crotonate, 2-sec.-butyl-4,6-dinitrophenyl-3,3-dimethylacrylate and 2-sec.-butyl-4,6-dinitrophenyl isopropyl carbonate; heterocyclic compounds, e.g. N-(1,1,2,2-tetrachloroethylthio)-tetrahydrophthalimide, N-trichloromethylthiotetrahydrophthalimide, N-trichloromethylthiophthalimide, 2-heptadecyl-2-imidazoline acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 5-ethoxy-3-trichloromethyl-1,2,4-thiadiazole, 2,3-dicyano-1,4-dithiaanthraquinone, 2-thio-1,3-dithio-(4,5-b)-quinoxaline, methyl 1-(butylcarbamoyl)-2-benzimidazole-carbamate, 2-methoxycarbonylamino-benzimidazole, 2-thiocyanatomethylthio-benzthiazole, 4-(2-chlorophenylhydrazono)-3-methyl-5-isoxazolone, pyridine-2-thio-1-oxide, 8-hydroxyquinoline and its copper salts, 2,3-dihydro-5-xarboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, 2,5-dimethyl-furan-3-carboxylic acid anilide, 2,5-dimethylfuran-3-carboxylic acid cyclohexylamide, 2-cyano-N-(ethylaminocarbonyl)-2-(methoxyimino)-acetamide, 2-methylbenzoic acid anilide, 2-iodo-benzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclododecyl-morpholine and its salts, DL-methyl-N-(2,6-dimethyl-phenyl)-N-furoyl(2)-alaninate, DL-N-(2,6-dimethyl-phenyl)-N-(2'-methoxyacetyl)-alanine methyl ester, diisopropyl 5-nitroisophthalate, 1-(1',2',4'-triazolyl-1')1-(4'-chlorophenoxy)-3,3-dimethylbutan-2-one, 1-(1',2',4'-triazolyl-1')-1-(4'-chlorophenoxy)-3,3-dimethylbutan-2-ol, N-(2,6-dimethylphenyl)-N-chloroacetyl-D,L-aminobutyrolactone, and N-(n-propyl)-N-(2,4,6-trichlorophenoxyethyl)-N'-imidazolylurea.

The following Example A demonstrates the biological action of the novel active ingredients. The compound 1-(2'-(2'',4''-dichlorophenyl)-2'-(2'''-propenyloxy)-ethyl-1H-imidazole disclosed in German Laid-Open Application DE-OS 2,063,857 was used for comparison purposes.

EXAMPLE A

Leaves of wheat seedlings of the "Jubilar" variety grown in pots are sprayed with aqueous emulsions prepared from 80% (wt%) active ingredient and 20% emulsifier, and dusted, after the sprayed-on layer has dried, with spores of wheat mildew (Erysiphe graminis var. tritici). The plants are then placed in a greenhouse at from 20° to 22° C. and from 75 to 80% relative humidity. The extent of fungus spread is assessed after 10 days.

| Compound from Ex. no. | Leaf attack after spraying with liquor containing compounds in amounts of | | |
|---|---|---|---|
|  | 0.012% | 0.006% | 0.003% |
| 5 | 2 | 2 |  |
| 6 | 2 | 2 |  |
| 7 | 2 | 2 |  |
| 8 | 2 | 2 |  |
| 9 | 2 | 2 |  |
| 10 | 2 | 2 |  |
| 13 | 1 | 2 |  |
| 15 | 2 | 2 |  |
| 17 | 0 | 0 | 0 |
| 18 | 1 | 1 |  |
| 19 | 0 | 2 |  |
| 20 | 1 | 1 |  |
| 21 | 2 | 2 |  |
| 26 | 1 | 1 |  |
| 27 | 0 | 0 | 0 |
| 31 | 0 | 2 |  |
| 43 | 1 | 1 |  |
| 46 | 0 | 0 | 0 |
| 47 | 0 | 0 | 3 |
| 48 | 0 | 0 | 0 |
| 49 | 0 | 0 | 0 |
| 51 | 2 | 2 |  |
| 52 | 2 | 2 |  |
| 53 | 2 | 2 |  |
| 56 | 1 | 2 | 3 |
| 57 | 0 | 1 | 1 |
| 58 | 0 | 0 | 0 |
| 59 | 0 | 0 | 1 |
| 60 | 0 | 1 | 1 |
| 65 | 0 | 0 | 1 |
| 66 | 0 | 0 | 0 |
| 67 | 0 | 0 | 0 |
| 68 | 0 | 0 | 0 |
| 69 | 0 | 0 | 0 |
| 70 | 0 | 0 | 1 |
| 71 | 0 | 0 | 0 |
| 72 | 0 | 2 | 3 |
| 73 | 0 | 0 | 2 |
| 74 | 0 | 0 | 0 |
| 75 | 1 | 1 | 2 |
| 76 | 0 | 0 | 1 |
| 77 | 0 | 0 | 0 |
| 78 | 1 | 1 | 3 |
| 79 | 1 | 1 | 3 |
| 80 | 0 | 0 | 1 |
| 84 | 0 | 0 | 1 |
| 86 | 0 | 0 | 0 |
| 87 | 0 | 0 | 0 |
| 88 | 0 | 0 | 0 |
| Comparative agent | 3 | 4 |  |
| Control (untreated) | 5 | | |

0 = no fungus attack, graduated down to 5 = total attack

The compounds according to the invention may also be used as agents for influencing plant growth. Their action is better than that of prior art growth regulators. The compounds are effective not only in monocotyledons, e.g., cereals, such as wheat, barley, rye, oats, rice and Indian corn, but also in dicotyledons, e.g., sunflowers, tomatoes, soybeans, grapes, cotton and rape, and various ornamentals, such as chysanthemums, poinsettias and hibiscus.

The following example demonstrates the action of the compounds according to the invention as plant growth regulators.

EXAMPLE B

To determine the growth-regulating properties of the compounds, test plants were grown in a substrate provided with sufficient nutrients in plastic vessels approx 12.5 cm in diameter.

The compounds were made up into aqueous formulations and sprayed on to the plants. The growth-regulating action observed was confirmed at the end of the experiment by measuring the growth height. These values were then compared with those for untreated plants. The compound CCC was used for comparison purposes:

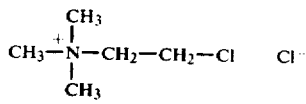

The reduction in growth height was accompanied by an intenser coloring of the waves. The increased chlorophyll content is indicative of an increased rate of photosynthesis, so that a higher yield may be expected.

The individual figures are given in the following table:

Soybeans; SRF 450 variety

Postemergence treatment; a duration of a expt.: 27 days

| Compound from Ex. no. | Appln. rate mg/vessel | Growth height % |
|---|---|---|
| — | — | 100 |
| CCC | 1.5 | 99.7 |
|  | 6.0 | 96.4 |
| 39 | 1.5 | 50.3 |
|  | 6.0 | 48.7 |
| 72 | 1.5 | 45.5 |
|  | 6.0 | 39.0 |
| 74 | 1.5 | 58.1 |
|  | 6.0 | 53.2 |
| 78 | 1.5 | 59.8 |
|  | 6.0 | 59.8 |
| 79 | 1.5 | 76.4 |
|  | 6.0 | 54.8 |

We claim:

1. A process for reducing the growth height of plants which comprises: applying to said plants or to the habitat of such plants an effective amount of a composition comprising a solid or liquid carrier and a compound of the formula I

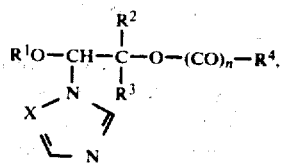

where $R^1$ is $C_{1-4}$-alkyl, $R^2$ is $C_{1-6}$-alkyl or unsubstituted or chlorine-substituted phenyl, $R^3$ is hydrogen, $C_{1-6}$-alkyl, $C_{2-6}$-alkenyl, $C_{2-6}$-alkynyl or unsubstituted or chlorine-substituted benzyl, $R^4$ is methyl, ethyl, propenyl, propynyl, unsubstituted or chlorine-substituted benzyl or, where $n=1$, may also be unsubstituted or chlorine-, trifluoromethyl- or nitro-substituted phenyl, X is CH or N and n is 0 or 1 or a plant-tolerated salt or metal complex thereof.

2. The process of claim 1, wherein n is 0.

3. The process of claim 1, wherein a salt or metal complex of a compound of the formula I that is tolerated by plants is used in the composition.

4. The process of claim 1, wherein in compound I, $R^1$, $R^3$ and $R^4$ are each $CH_3$, $R^2$ is 2,4-dichlorophenyl, n is 0 and X is N.

5. The process of claim 1, wherein in compound I, $R^1$ and $R^4$ are each $CH_3$, $R^2$ is 2,4-dichlorophenyl, $R^3$ is H, n is 0 and X is N.

6. The process of claim 1 wherein the compound is allowed to act on wheat, barley, rye, oats, rice or Indian corn.

7. The process of claim 1 wherein the compound is allowed to act on sunflowers, tomatoes, soybeans, grapes, cotton or rape.

8. The process of claim 1 wherein the compound is allowed to act on chrysanthemums, poinsettias or hibiscus.

9. The process of claim 1 wherein the compound is allowed to act on rice plants.

* * * * *